United States Patent
Cascone et al.

(10) Patent No.: US 6,579,248 B1
(45) Date of Patent: Jun. 17, 2003

(54) BIOFEEDBACK DEVICE

(76) Inventors: Roberta L. Cascone, 7 Cheshire Rd., Wallyford, CT (US) 06492; Steven D. White, 15 Carriage Dr., No Haven, CT (US) 06473

( * ) Notice: Subject to any disclaimer, the term of this patent is extended or adjusted under 35 U.S.C. 154(b) by 119 days.

(21) Appl. No.: 09/803,629

(22) Filed: Mar. 9, 2001

(51) Int. Cl.⁷ .............................................. A61B 5/103
(52) U.S. Cl. ................ 600/587; 600/594; 340/573.7
(58) Field of Search .................... 600/587, 594; 340/573.7

(56) References Cited

U.S. PATENT DOCUMENTS

| | | | | |
|---|---|---|---|---|
| 3,978,851 A | * | 9/1976 | Sobel | 600/38 |
| 4,007,733 A | * | 2/1977 | Celeste et al. | 128/905 |
| 4,055,168 A | | 10/1977 | Miller et al. | 600/594 |
| 4,730,625 A | * | 3/1988 | Fraser et al. | 128/905 |
| 4,750,480 A | * | 6/1988 | Jenness | 128/101.1 |
| 4,871,998 A | * | 10/1989 | Chaillou | 200/61.52 |
| 4,914,423 A | | 4/1990 | Fernandez | 340/573.4 |
| 5,263,491 A | * | 11/1993 | Thornton | 600/483 |
| 5,304,984 A | * | 4/1994 | Roldan | 340/407.1 |
| 5,375,842 A | * | 12/1994 | Plottner | 340/573.7 |
| 5,402,107 A | * | 3/1995 | Rencavage | 340/573.7 |
| 6,119,516 A | * | 9/2000 | Hock | 600/547 |

* cited by examiner

*Primary Examiner*—Patrick Brinson
(74) *Attorney, Agent, or Firm*—Bachman & LaPointe, P.C.

(57) ABSTRACT

The present invention relates to a biofeedback device for providing a wearer with instantaneous and continuous information about their posture. The device comprises a sensor unit affixed to the wearer, an attachment element affixed to the wearer, an elastic cord extending between the sensor unit and the attachment element, and movement of the elastic cord due to incorrect posture actuating an indicating device. The biofeedback device further comprises a power pack separate from the sensor unit.

20 Claims, 3 Drawing Sheets

BIOFEEDBACK DEVICE

BACKGROUND OF THE INVENTION

The present invention relates to a biofeedback device which provides instantaneous and continuous feedback to a wearer about their posture. The device of the present invention allows a wearer to become aware of present posture and enables the wearer to change positions via cortical control.

Understanding the biomechanical influence on physical function is key in the treatment of musculoskeletal disabilities and the enhancement of athletic performance. In rehabilitation, physical training and biofeedback are extensively utilized in muscle reeducation and relaxation.

Over the years, a number of posture training devices have been developed. For example, U.S. Pat. No. 4,055,168 to Miller et al. illustrates one posture training device which includes an electrically conductive plate divided into two contact zones and slidable upon a support base of one housing section of the device. One end of the plate is operatively connected to a body harness cable extending around the longitudinal axis of the body from the pubis to the scapula, while the other end of the plate is electrically connected to spring-biased cable winding mechanisms. The two zones of the plate are separated and electrically insulated from each other by a predetermined gap which extends along the plate with a predetermined curvature or rectilinearly at a constant slope, and another slidable plate, having a contact member disposed therein, is similarly provided within another housing section with a harness cable at one end thereof, which cable extends laterally about the chest area of the patient, and is operatively, electrically connected to a spring biased cable winding mechanism at the other end thereof through means of the contact member. The electrically conductive plate and contact member of the second plate serve as a single-pole, double throw switch and common contact member respectively, and the relative movement of both plates, as defined by the contact member and the zones of the electrically conductive plate, serve to open or close a signal emitting circuit so as to accurately indicate the assumption of a proper or improper postural position or condition by the patient, independent of the respiration of the patient. In another embodiment of the Miller et al. device, rotary potentiometers are used.

Another posture training device is illustrated in U.S. Pat. No. 4,871,998 to Chaillou. The posture training device comprises a belt worn on the body of the user to remind the user to maintain good posture. The posture belt has a buzzer housing and an elongated belt. One end of the belt is detachably connected to the buzzer housing and the other end of the belt is connected to structure for actuating the buzzer alarm that forms part of the buzzer alarm circuit mounted within the buzzer housing. The buzzer alarm is actuated when the belt is distended due to improper posture.

Still another belt posture training device is shown in U.S. Pat. No. 4,914,423 to Fernandez. The Fernandez device includes a housing which contains an alarm and sensing mechanism, a one-piece belt fastened at one end of the housing and attached to one of the legs of a four-sided round-wire ring at the other end via a flat hook, the length of the belt being adjustable via a slide ring. When the wearer's waist is in a contracted position, there is no alarm since the circuit is not completed; however, when the waist is expanded and the belt has been preadjusted such that in this enlarged condition the leaf spring completes the electric circuit and actuates the alarm in the housing.

Yet another belt posture training device is illustrated in U.S. Pat. No. 5,304,984 to Roldan. In this device, a predetermined amount of tension in a belt around the wearer's waist closes a switch and activates a buzzer, vibration motor, or other indicating means in the belt buckle of the belt. The amount of tension required to achieve the closing of the switch is adjustable.

Despite the existence of these devices, there remains a need for a device which provides instantaneous and continuous feedback to a wearer about their posture.

SUMMARY OF THE INVENTION

Accordingly, it is a principal object of the present invention to provide a feedback device which provides instantaneous and continuous feedback to the wearer about their posture.

It is a further object of the present invention to provide a feedback device as above which is compact and self-contained and which can be applied and used during physical activity and training.

The foregoing objects are attained by the feedback device of the present invention.

In accordance with the present invention, the feedback device comprises a sensor unit affixed to the wearer, an attachment element affixed to the wearer, an elastic cord extending between the sensor unit and the attachment element, and movement of the elastic cord due to incorrect posture actuating an indicating device. The biofeedback device further comprises a power pack separate from the sensor unit.

Other details of the biofeedback device of the present invention, as well as other objects and advantages attendant thereto, are set forth in the following detailed description and the accompanying drawings wherein like reference numerals depict like elements.

DETAILED DESCRIPTION OF THE PREFERRED EMBODIMENT(S)

Figure 1:
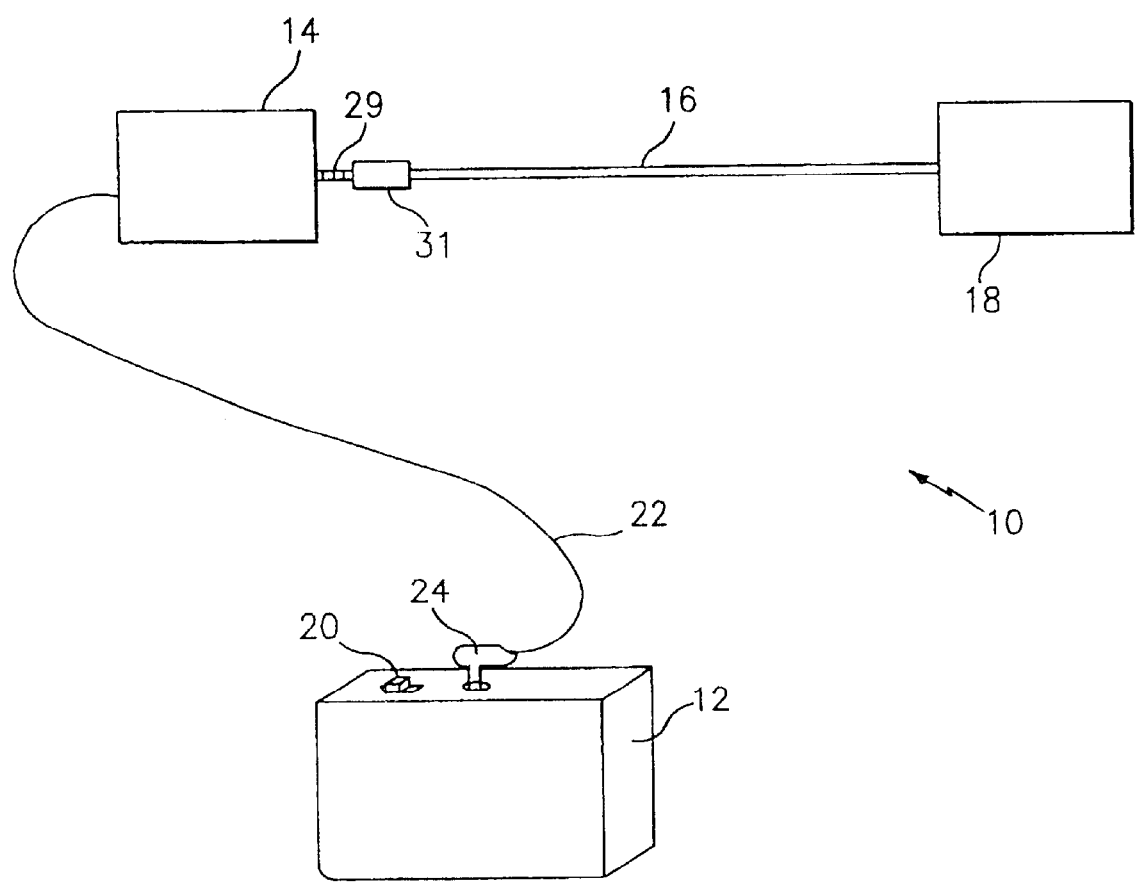
FIG. 1 is a schematic representation of the biofeedback device of the present invention.
Figure 2:
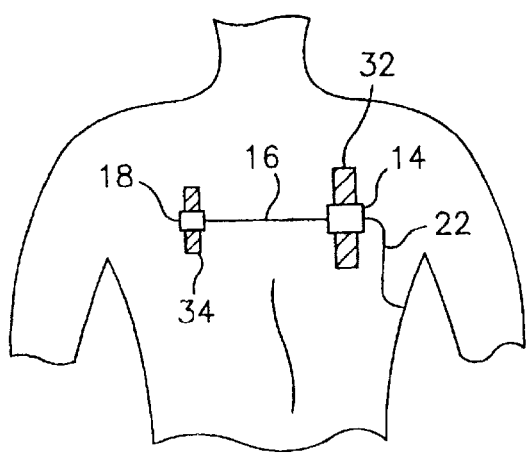
FIG. 2 is a schematic representation showing how the biofeedback device of the present invention can be applied to a wearer.

Referring now to FIG. 1 of the drawings, the miniature biofeedback device 10 includes a power pack 12, a miniature sensor unit 14 incorporating an indicator device, an elastic cord 16 and an attachment element 18. The power pack 12 provides 3.0 volts to the sensor unit 14 and includes an on-off switch 20. Power is supplied to the sensor unit 14 through an insulated two conductor wire 22 terminating in a miniaturized plug 24. The sensor unit 14 incorporates a switch 26 that is activated when the elastic cord 16 is pulled by the action of the wearer. When the switch 26 is activated, power is supplied to an indicating device 28, such as a vibration device or buzzer, incorporated in the sensor unit 14 or in the power pack 12 to alert the wearer that undesired motion has taken place. The elastic cord 16 is attached to the sensor unit 14 by a threaded sleeve 31 which is screwed onto a threaded end 29 of the sensor unit 14 that allows elastic cords of various lengths to be used. As shown in FIG. 2, the sensor unit 14 may be attached to the wearer by adhesive tape 32 positioned over the unit 14. If desired, the sensor unit 14 may be affixed to the wearer using double sided adhesive tape in lieu of the tape 32. The double sided adhesive tape may be applied to a wall of the sensor unit to be positioned adjacent the wearer. The attachment element 18 may be adhesively affixed to the wearer using tape 34 positioned over the element 18. Here again, double sided tape may be utilized in lieu of the tape 34 to affix the attachment element 18 to the wearer. The attachment element 18 is affixed to the wearer at a point such that the sensor unit 14 can detect undesired motion.

Figure 5:
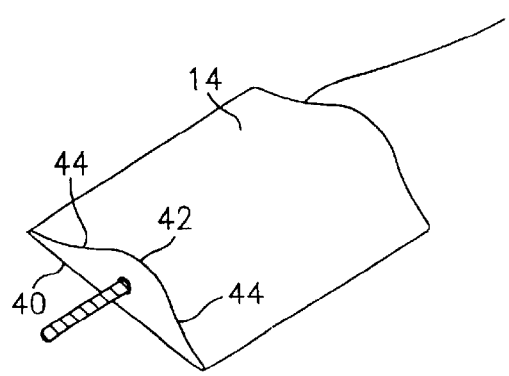
FIG. 5 is a perspective view of the sensor unit used in the biofeedback device of the present invention.

Referring to FIG. 5, the sensor unit 14 is preferably shaped so that it has a flat base 40, an arcuately shaped apex portion 42, and two sloping sides 44. The sensor unit 14 is small enough to be worn on the wearer's body with minimum disturbance, and is approximately 3 cm×2.4 cm×0.8 cm. The sloping sides 44 helps insure that the tape used to hold the unit 14 on the wearer adheres firmly.

Figure 3:
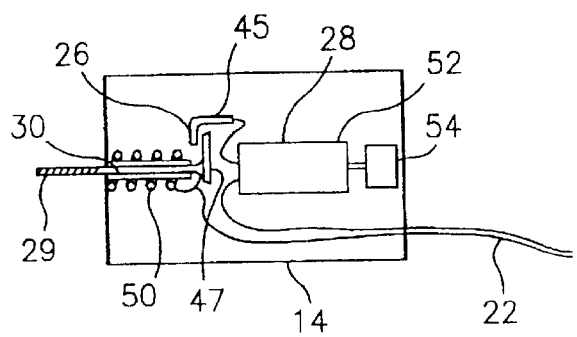
FIG. 3 is a sectional view of a sensor unit used in the biofeedback device of FIG. 1.

Referring now to FIG. 3, the sensor unit 14 incorporates an electric switch 26 that is activated by a pull on the threaded end 29. Movement of the threaded end 29 is restrained by a coil spring 50 which surrounds a portion of the arm 30. The spring 50 resists the pull on the elastic cord 16. The switch 26 has a first contact plate 45 which is electrically connected to the indicator device 28 and a second contact plate 47 connected to the arm 30. Activating the switch 26 by causing first contact plate 45 to contact second contact plate 47 in turn causes current to flow to the indicator device 28. In a preferred arrangement, the indicating device 28 comprises a vibration device which includes a miniature electric motor 52 and an eccentric rotor 54 attached to the motor 52. Rotation of the eccentric rotor 54 causes a vibration that is transmitted to the sensor unit 14 and to the wearer.

If desired, the switch 26 may be arranged to operate in the opposite manner, activating when tension on the elastic cord 16 is relaxed rather than when the elastic cord is pulled. This configuration can be used in physical training of relaxation techniques, or when the specific application requires this type of activation.

In yet another variation, the switch 26 may be arranged to operate in both directions activating when tension on the elastic cord is relaxed and when the elastic cord is pulled. This configuration trains the user to maintain a specific position.

Figure 4:
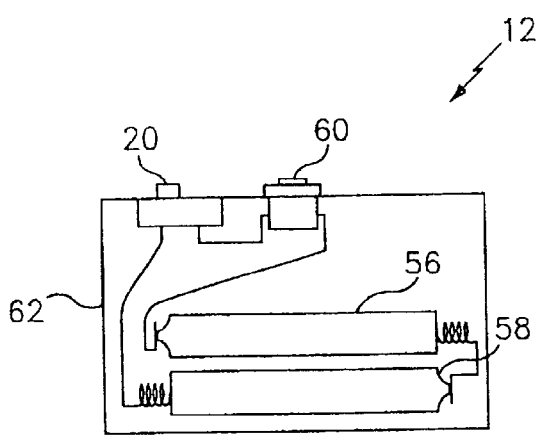
FIG. 4 is a sectional view of a power pack used in the biofeedback device of FIG. 1.

Referring now to FIG. 4, the power pack 12 contains two 1.5 volt batteries 56 and 58, the on-off switch 26 and a jack 60 for accepting the plug 24 from the sensor unit. The pack 12 comprises a compact plastic case 62 for accommodating the foregoing and which may be sized to fit in a user's pocket. If desired, the case 62 may be provided with a clip to allow it to be attached to a wearer's belt.

FIG. 2 illustrates a typical installation of the device 10 of the present invention. The sensor unit 14 is secured to the medial border of the right scapula and the attachment element 18 is secured to the medial border of the left scapula. The insulated wire 22 may be run under the wearer's clothing to the power pack 12 which may be positioned on a belt worn by the wearer or in a pocket of the wearer's clothes. The device 10 is adjusted on the wearer to position the scapula in optimal biomechanical posture to allow for maximal function during a given activity. When the wearer positions the scapula in the desired posture, the elastic cord 16 is snug and the switch 36 in the sensor unit 14 is not activated. If the wearer allows the scapula to move award, away from the spine, the elastic cord 16 tightens, pulling on the sensor unit 14, and causing the indicating device 28 to vibrate or buzz, alerting the wearer. The response is instantaneous and continuous, affording feedback to the wearer for correction of undesired posture.

Figure 8:
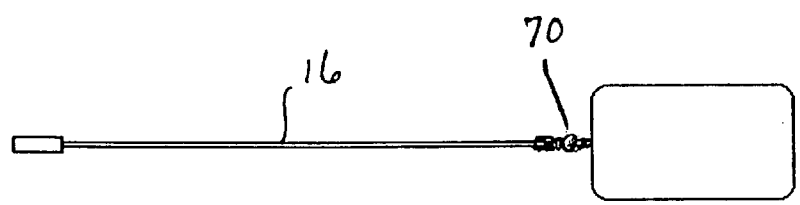
FIG. 8 illustrates a biofeedback device having a swivel attached to an elastic cord.

In a variation of the device 10, as shown in FIG. 8, the elastic cord 16 incorporates a swivel 70 at the attachment to the attachment element 18. This allows for rotation of the threaded sleeve 31 while the device 10 is attached to the wearer to adjust the amount of motion required to activate the device 10.

Figure 6:
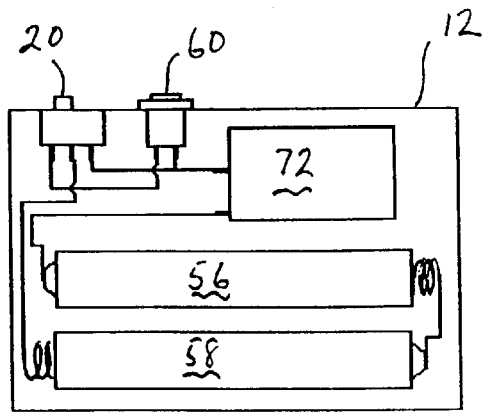
FIG. 6 is a sectional view of an alternative embodiment of a power pack.

The power pack 12, if desired, as shown in FIG. 6, may contain a buzzer 72 to alert a therapist as well as the wearer when undesired motion is detected. A switch or switches may be provided so that the user can select the desired mode of operation.

Figure 7:
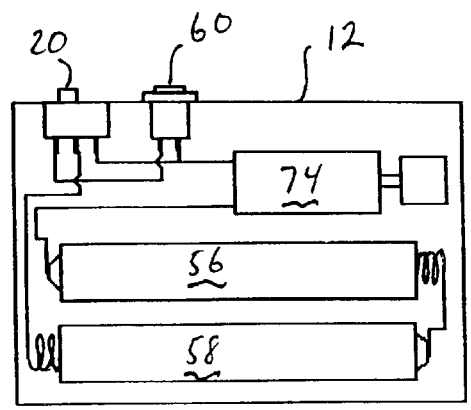
FIG. 7 is a sectional view of yet another power pack embodiment.

In yet another variation of the device of the present invention, as shown in FIG. 7, a vibration device 74 may be positioned in the power pack 12 in lieu of the sensor unit 14. Such a configuration allows a more compact sensor unit, however, the vibration is less easy to detect by the wearer and is not connected to the area of the body where motion is taking place.

In still another variation of the device of the present invention, the indicating device 28 is omitted from the sensor unit and replaced by a buzzer in the power pack 12.

The device 10 of the present invention provides a number of advantages. First, it can be easily and comfortably be worn by a wearer during physical activity. Second, the elastic cord 16 allows free movement by the wearer without restraint by the device 10, and allows the device 10 to remain attached to the wearer over a wide range of motion. Third, the use of a vibration device to alert the wearer of undesired motion allows the device to be worn during normal activity without disturbing others around the wearer.

Other advantages to the biofeedback device of the present invention is that its small size allows the sensor unit 14 to be mounted directly to the body with adhesive tape and allows the sensor unit 14 to be worn under the clothing of the user so as to be unobtrusive during normal activity. The small size of the device 10 of the present invention is directly attributable to the use of a power pack 12 separate from the sensor unit 14. The threaded connection at the sensor unit allows very fine adjustments of the operation of the device 10. Each turn of the threaded end 29 of the arm 30 changes the length of the elastic cord 16 by only about 0.5 mm. The swivel 70 at the attachment element 18 allows for adjustment while the device is installed without removing the tape used to hold it on. Tests have shown that the swivel 70 does not rotate during operation of the unit, so the adjustment does not shift.

While it is preferred to attach the device 10 to the wearer using adhesive tape, any suitable means known in the art, including adhesive gels and other suitable adhesives, may be used to affix the sensor unit 14 and the attachment unit 18 to the wearer's body.

There has been provided in accordance with the present invention a miniature biofeedback device which fully satisfies the means, objects and advantages set forth hereinbefore. While the present invention has been described in the context of specific embodiments thereof, other alternatives, variations, and modifications will become apparent to those skilled in the art having read the foregoing description. Therefore, it is intended to embrace those alternatives, variations, and modifications which fall within the broad scope of the appended claims.

What is claimed is:

1. A biofeedback device comprising:
   a sensor unit affixed to said wearer;
   an attachment element affixed to said wearer;
   an elastic cord extending between said sensor unit and said attachment element;
   means for indicating incorrect posture by movement of said cord due to incorrect posture; and
   said sensor unit being secured to the medial border of a first one of the wearer's scapulas and the attachment element being secured to the medial border of a second one of the wearer's scapulas.

2. A biofeedback device according to claim 1, further comprising said sensor unit being adhesively affixed to said wearer.

3. A biofeedback device according to claim 1, further comprising said sensor unit being affixed to said wearer by a piece of adhesive tape.

4. A biofeedback device according to claim 1, further comprising said attachment element being adhesively affixed to said wearer.

5. A biofeedback device according to claim 1, further comprising said attachment element being affixed to said wearer by a piece of adhesive tape.

6. A biofeedback device according to claim 1, further comprising said elastic cord being connected to a switch connected to said indicating means and said elastic cord causing said switch to actuate said indicating means when incorrect posture occurs.

7. A biofeedback device according to claim 6, wherein said indicating means comprises a vibrating device in said sensor unit.

8. A biofeedback device according to claim 7, wherein said vibrating device comprises an electric motor and an eccentric rotor.

9. A biofeedback device according to claim 8, further comprising a power pack containing a source of electrical power and conducting wires extending between said power pack and said electric motor and said switch.

10. A biofeedback device according to claim 9, wherein said power pack is separate from said sensor unit.

11. A biofeedback device according to claim 9, wherein said power pack has an on-off switch.

12. A biofeedback device according to claim 11, wherein said electrical power source comprises a pair of batteries in said power pack.

13. A biofeedback device comprising:
    a sensor unit affixed to said wearer;
    an attachment element affixed to said wearer;
    an elastic cord extending between said sensor unit and said attachment means;
    means for indicating incorrect posture in response to movement of said cord due to said incorrect posture;
    wherein said elastic cord is connected to a switch connected to said indicating means and said elastic cord causing said switch to actuate said indicating means when incorrect posture occurs;
    said switch comprising a first contact plate, a second contact plate connected to an arm with a threaded end, a coil spring within said sensor unit surrounding a portion of said arm, and said elastic cord being connected to said threaded end of said arm.

14. A biofeedback device according to claim 13, further comprising a swivel attached to said elastic cord at an attachment of said elastic cord to said attachment element to allow the threaded end of said arm to rotate, when said device is attached to said wearer, to adjust the amount of motion required to actuate the device.

15. A biofeedback device according to claim 1, wherein tension in said elastic cord actuates said indicating means.

16. A biofeedback device comprising:
    a sensor unit affixed to said wearer;
    an attachment element affixed to said wearer;
    an elastic cord extending between said sensor unit and said attachment element;
    means for indicating incorrect posture by movement of said cord due to incorrect posture; and
    said elastic cord actuating said indicating means when tension in said elastic cord is relaxed.

17. A biofeedback device comprising:
    a sensor unit affixed to said wearer;
    an attachment element affixed to said wearer;
    an elastic cord extending between said sensor unit and said attachment element;
    means for indicating incorrect posture by movement of said cord due to incorrect posture; and
    said indicating means being actuated when tension in said elastic cord is relaxed and when said elastic cord is pulled.

18. A biofeedback device according to claim 1, further comprising a power pack separate from said sensor unit and said indicating means comprising a buzzer in said power pack.

19. A biofeedback device according to claim 1, further comprising a power pack separate from said sensor unit and said indicating means comprising a vibrating device in said power pack.

20. A biofeedback device comprising:
    a sensor unit affixed to said wearer;
    an attachment element affixed to said wearer;
    an elastic cord extending between said sensor unit and said attachment element;
    means for indicating incorrect posture by movement of said cord due to incorrect posture; and
    said sensor unit having a planar base, an apex portion, and two sloping sides extending between said apex portion and said base.

* * * * *